United States Patent

Hell et al.

[11] Patent Number: 5,841,831
[45] Date of Patent: Nov. 24, 1998

[54] X-RAY COMPUTED TOMOGRAPHY APPARATUS

[75] Inventors: Erich Hell, Erlangen; Peter Schardt, Roettenbach; Guenter Schwierz, Neunkirchen, all of Germany

[73] Assignee: Siemens Aktiengesellschaft, Munich, Germany

[21] Appl. No.: 847,622

[22] Filed: Apr. 28, 1997

[30] Foreign Application Priority Data

May 9, 1996 [DE] Germany ............... 196 18 749.4

[51] Int. Cl.$^6$ ............................ G01N 23/00
[52] U.S. Cl. ............. 378/19; 378/4; 378/12
[58] Field of Search ............... 378/19, 4, 12

[56] References Cited

U.S. PATENT DOCUMENTS 4,665,539  5/1987  Geluk .
5,712,889  1/1998  Lanyara et al. ............... 378/19

*Primary Examiner*—Craig E. Church
*Attorney, Agent, or Firm*—Hill & Simpson

[57] ABSTRACT

In an x-ray computed tomography apparatus the source of X-rays and the detector are able to scan a volume of the examination subject in a short time. The X-ray source contains an anode that is elongated in the z-direction, on which the focus travels by a controlled deflection of an electron beam. A primary beam diaphragm is displaced synchronously with the focus movement along the anode. The diaphragm forms a pyramid-shaped X-ray beam which always fully strikes the detector but does not overshot the detector. The detector is formed by a matrix of detector elements.

1 Claim, 2 Drawing Sheets

X-RAY COMPUTED TOMOGRAPHY APPARATUS

BACKGROUND OF THE INVENTION

1. Field of the Invention

The present invention is directed to a computed tomography system of the type having an anode extending along the z-axis of the system, around which an x-ray source and a detector rotate for scanning an examination subject.

2. Description of the Prior Art

In known computed tomography systems, scanning of the subject under examination ensues by means of a fan-shaped X-ray beam that is emitted at different angles around a patient by a source of X-ray radiation and strikes a detector formed by an array of detector elements. For scanning several parallel slices of the subject under examination, given the use of a surface detector (detector matrix), an elongated anode can be provided in the X-ray source, this anode extending in the direction of the system axis around which the X-ray source and the detector are rotated. The focus is moved along such an anode in the direction of the system axis (z-axis).

German OS 32 22 030 describes an X-ray computed tomography apparatus wherein the conventional rotational motion about the system axis of the measurement arrangement of the X-ray source and the detector, for the transillumination of the examination from various directions (angles), is eliminated by the use of a stationary row-type detector and a source of X-ray radiation having an elongated anode, on which the focus is electronically moved, so that the flat X-ray radiation beam strikes the detector from various directions. There is no discussion in this document, however, as to how a volume scanning of the examination subject could ensue using such a system.

SUMMARY OF THE INVENTION

An object of the present invention is to provide an X-ray tomography apparatus with which a rapid scanning of a volume of the examination subject ensues using an X-ray source with an anode elongated in the direction of the z-axis.

The above object is achieved in accordance with the principles of the present invention in a computed tomography apparatus having an x-ray source and a detector which rotate around the z-axis to scan an examination subject, the x-ray source containing an anode extending along the z-axis, along which the focus, from which the x-ray beam is emitted, is caused to travel by a controlled deflection of an electron beam. The system also includes a primary beam diaphragm which is displaced synchronously with the focus movement along the anode. The diaphragm forms a pyramid-shaped x-ray beam which always fully strikes the detector, but does not overshoot the detector.

In the inventive tomography apparatus, a volume can be acquired without the necessity of moving the patient during the volume scan. As a result, volume exposures are possible with only one rotation of the source and detector.

DESCRIPTION OF THE PREFERRED EMBODIMENT

Figure 1:
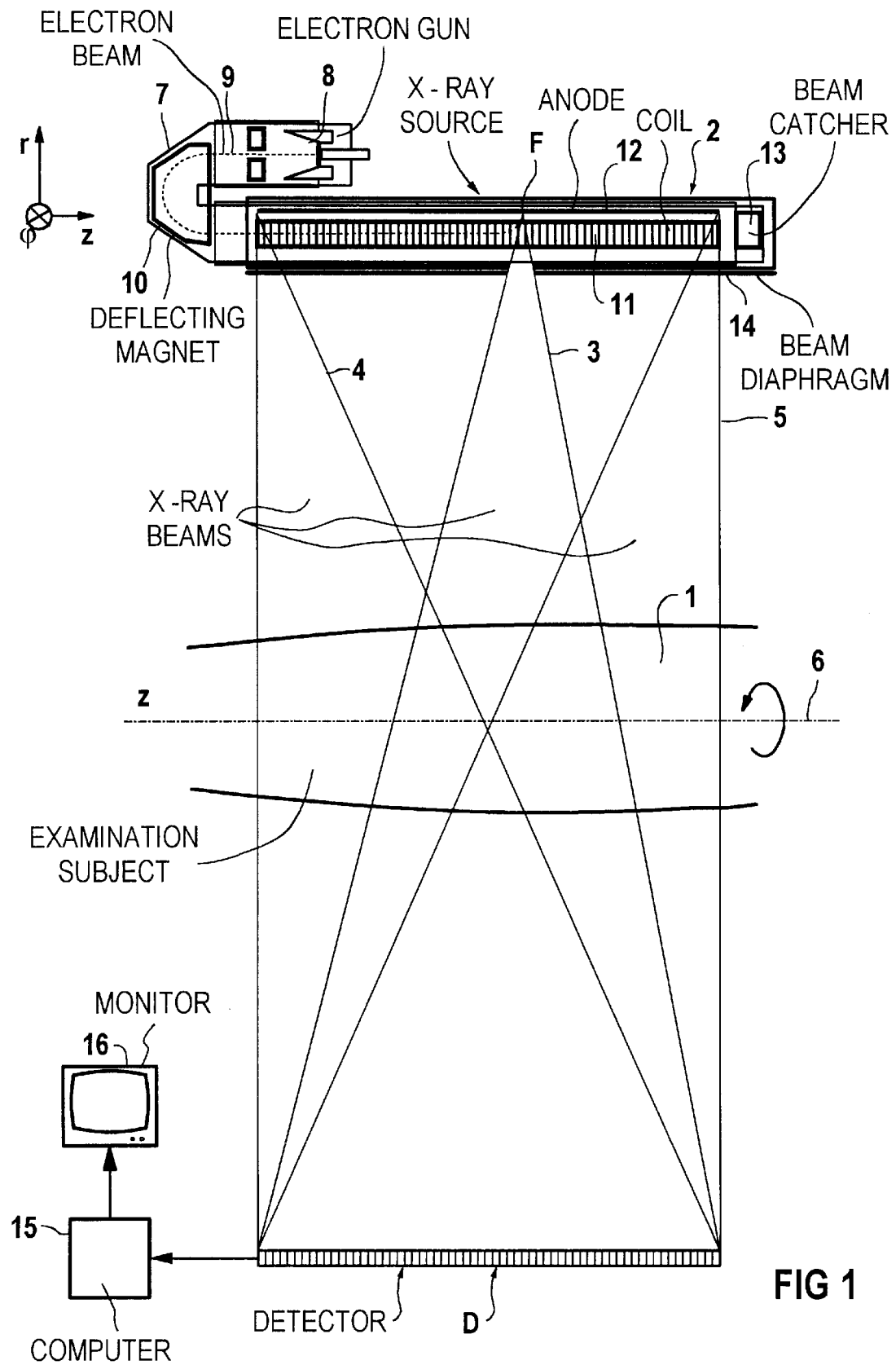
FIG. 1 is a schematic illustration of the basic components of a computed tomography apparatus constructed according to the present invention.

FIG. 1 shows an examination subject 1 being examined by a measurement system formed by an X-ray source 2 and a detector D. For this purpose, the X-ray source 2 emits a pyramid-shaped X-ray beam 3 (and 4 and 5, respectively at different z-positions along an anode 12 extending along the z-axis), which penetrates the examination subject 1 and the attenuated beam then strikes the detector D. The detector D is extended in the direction of the system axis 6 (z-axis), and is formed by a matrix of detector elements. To scan the examination subject 1, the X-ray source 2 and the detector D are rotated around the system axis 6. A computer 15 computes image information from the thereby formed output signals of all of the detector elements of the detector D, so that an image of the examined body part can be reproduced on a monitor 16.

The X-ray source 2 contains, in a housing 7, an electron gun 8 that emits an electron beam 9, the electron beam 9 being deflected 180° by a deflecting magnet 10 and passing through a coil arrangement 11. The coil arrangement 11 includes of a row of magnetic coils that can be driven individually, so that a magnetic field of traveling waves can be produced, by means of which the focus F can be deflected along the anode 12, in the longitudinal direction thereof. A beam catcher 13 prevents the electron beam 9 from exiting the X-ray source 2.

By means of the magnetic field of traveling waves, the focus F travels over the entire length of the anode 12. A primary beam diaphragm 14 is displaced along the anode 12 synchronously with this motion, the diaphragm 14 forming the X-ray beam into a pyramid shape, so that it does not overshoot the detector D. During the displacement of the primary beam diaphragm 14, the X-ray beams 4 and 5 emitted at the ends of the anode 12 are prevented from overshooting the detector D at those locations.

Figure 2:
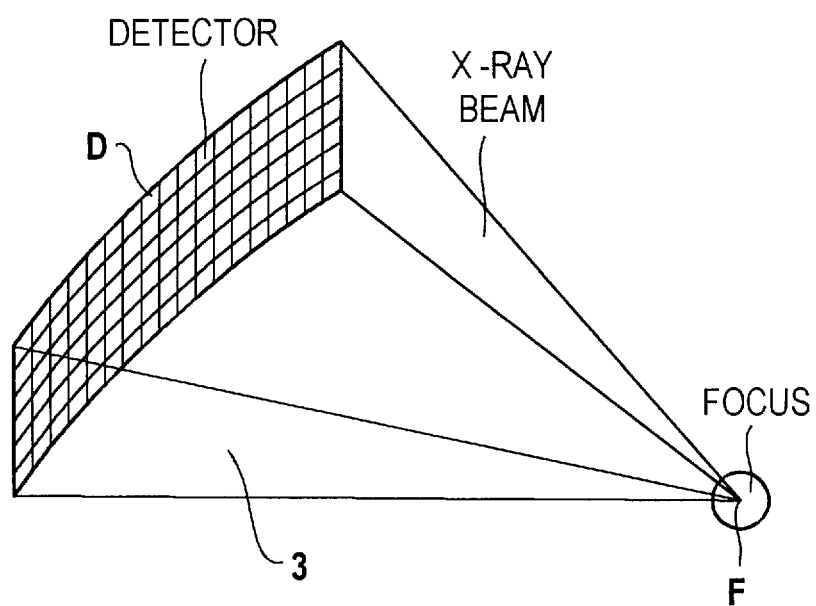
FIG. 2 shows the X-ray beam in the computed tomography apparatus of FIG. 1, in a perspective view.

The middle or central X-ray beam 3 is shown in more detail in FIG. 2. FIG. 2 shows that the beam propagates a pyramid shape and strikes the detector D fully without overshooting it.

Although modifications and changes may be suggested by those skilled in the art, it is the intention of the inventor to embody within the patent warranted hereon all changes and modifications as reasonably and properly come within the scope of her contribution to the art.

We claim as our invention:

1. An x-ray computed tomography apparatus having a system axis, said apparatus comprising:

a radiation detector;

an x-ray source having an anode extending parallel to said system axis, an electron gun which emits an electron beam, and deflection means for deflecting said electron beam onto said anode at a focus which moves along said anode parallel to said system axis;

a primary radiation diaphragm disposed between said anode and said system axis;

means for conducting a scan of an examination subject stationarily disposed parallel to said system axis by rotating said x-ray source and said detector around said system axis and moving said primary radiation diaphragm parallel to said system axis synchronously with movement of said focus on said anode for causing a pyramid-shaped x-ray beam to be emitted through said primary radiation diaphragm which always fully strikes said detector, said detector generating electrical signals as a result of x-rays incident thereon;

computer means for reconstructing an image of a selected volume of said examination subject from said electrical signals; and display means for displaying said image.

* * * * *